(12) United States Patent
Seward et al.

(10) Patent No.: US 9,149,497 B2
(45) Date of Patent: Oct. 6, 2015

(54) METHODS AND SYSTEMS FOR TREATING ISCHEMIC TISSUES

(75) Inventors: Kirk Patrick Seward, San Francisco, CA (US); Lynn Mateel Barr, Lafayette, CA (US); Robert Cafferata, Santa Rosa, CA (US)

(73) Assignee: Mercator MedSystems, Inc., San Leandro, CA (US)

( * ) Notice: Subject to any disclaimer, the term of this patent is extended or adjusted under 35 U.S.C. 154(b) by 950 days.

(21) Appl. No.: 12/239,589

(22) Filed: Sep. 26, 2008

(65) Prior Publication Data

US 2009/0142306 A1 Jun. 4, 2009

Related U.S. Application Data

(63) Continuation of application No. 10/829,905, filed on Apr. 21, 2004, now abandoned.

(60) Provisional application No. 60/465,013, filed on Apr. 22, 2003.

(51) Int. Cl.
*A01N 63/00* (2006.01)
*A61K 35/28* (2015.01)
*A61K 35/54* (2015.01)

(52) U.S. Cl.
CPC .................. *A61K 35/28* (2013.01); *A61K 35/54* (2013.01)

(58) Field of Classification Search
None
See application file for complete search history.

(56) References Cited

U.S. PATENT DOCUMENTS

| | | | |
|---|---|---|---|
| 4,513,007 A * | 4/1985 | de Courten et al. | 514/555 |
| 5,486,359 A | 1/1996 | Caplan et al. | |
| 5,591,625 A | 1/1997 | Gerson et al. | |
| 5,602,301 A | 2/1997 | Field | |
| 6,099,832 A | 8/2000 | Mickle et al. | |
| 6,283,947 B1 | 9/2001 | Mirzaee | |
| 6,387,369 B1 | 5/2002 | Pittenger et al. | |
| 6,730,313 B2 * | 5/2004 | Helmus et al. | 424/423 |
| 7,744,584 B2 * | 6/2010 | Seward et al. | 604/510 |
| 2002/0001581 A1 * | 1/2002 | Lynch et al. | 424/93.21 |
| 2002/0182186 A1 | 12/2002 | Loeb | |
| 2003/0171734 A1 * | 9/2003 | Seward et al. | 604/506 |
| 2006/0252150 A1 * | 11/2006 | Cheng | 435/372 |

OTHER PUBLICATIONS

Penn MS et al. 2012. Adventitial delivery of an allogeneic bone marrow-derived adherent stem cell in acute myocardial infarction: Phase I clinical study. Circ Res 110: 304-311.*
Leistner DM et al. 2012. Novel avenues for cell therapy in acute myocardial infarction. Circ Res 110: 195-197.*
Zeng L et al. 2007. Bioenergetic and Functional Consequences of Bone Marrow-Derived Multipotent Progenitor Cell Transplantation in Hearts With Postinfarction Left Ventricular Remodeling. Circ 115: 1866-1875.*
Zeng L et al. 2006. Multipotent adult progenitor cells from swine bone marrow. Stem Cells 24: 2355-2366.*
"Adventitia" and "perivascular." Medline Plus Merriam-Webster Medical Dictionary. Available online at <http://www.merriam-webster.com/medlineplus/adventitia> and <http://www.merriam-webster.com/medlineplus/perivascular>. Accessed Sep. 11, 2014. 2 pages.*
Assmus et al., "Transplantation of Progenitor Cells and Regeneration Enhancement in Acute Myocardial Infarction (TOPCARE-AMI)," *Circulation* 2002; 106: 3009-3017.
Custom Needle Gauge and Length [online]. Hamilton Company [retrieved on Feb. 27, 2007]. <<http://www.hamiltoncompany.com/syringes/gaugeindex.asp>>.
Fuchs et al., "Transendocardial Delivery of Autologous Bone Marrow Enhances Collateral Perfusion and Regional Function in Pigs With Chronic Experimental Myocardial Ischemia". *JACC*, 2001; 37(6): 1726-1732.
Hagege et al., "Viability and differentiation of autologous skeletal myoblast grafts in ischaemic cardiomyopathy", *Lancet* 2003; 361: 91-92.
Jackson et al., "Regeneration of ischemic cardiac muscle and vascular endothelium by adult stem cells," *J. Clin. Invest.*, Jun. 2001; 107(11): 1395-1402.
Kawamoto et al., "Intramyocardial transplantation of autologous endothelial progenitor cells for therapeutic neovascularization of myocardial ischemia," *Circulation*, 2003; 107:461-468.
Kawamoto et al., "Therapeutic potential of ex vivo expanded endothelial progenitor cells for myocardial ischemia," *Circulation*. 2001; 103: 634-637.
Kocher et al., "Neovascularization of ischemic myocardium by human bone-marrow-derived angioblasts prevents cardiomyocyte apoptosis, reduces remodeling and improves cardiac function". *Nature Medicine*, Apr. 2001; 1(4): 430-36.
Li et al., "Autologous Porcine Heart Cell Transplantation Improved Heart Function After a Myocardial Infarction," *J Thorac Cardiovasc Surg* 2000;119:62-068.
Merriam-Webster MedlinePlus Medical Dictionary definition of "adventitia" [retrieved Feb. 27, 2007]. Retrieved from the Internet: <<http://www2.merriam-webster.com/cgi-bin/mwmednlm?book=Medical&va=adventitia>.
Merriam-Webster MedlinePlus Medical Dictionary definition of "peri-" [retrieved Feb. 27, 2007]. Retrieved from the Internet:<<http://www2.merriam-webster.com/cgi-bin/mwmednlm?book=Medical& va=peri->.
Merriam-Webster MedlinePlus Medical Dictionary definition of "perivascular" [retrieved Feb. 27, 2007]. Retrieved from the Internet: <<http://www2.merriam-webster.com/cgi-bin/mwmednlm?book=Medical& va=perivascular>>.
Merriam-Webster Online dictionary definition of "adjacent." Retrieved from the Internet at <<http://mw1.merriamwebster.com/dictionary/adjacent>> on Sep. 21, 2007. 1 page.
Min et al., "Significant improvement of heart function by cotransplantation of human mesenchymal stem cells and fetal cardiomyocytes in postinfarcted pigs," *Ann Thorac Surg* Nov. 2002; 74(5): 1568-75.
Orlic et al., "Bone marrow cells regenerate infracted myocardium". *Nature* Apr. 5, 2001; 410 (6829): 701-5.

(Continued)

*Primary Examiner* — Lora E Barnhart Driscoll
(74) *Attorney, Agent, or Firm* — Wilson Sonsini Goodrich & Rosati

(57) ABSTRACT

Methods and systems for regenerating damaged tissue rely on direct injection of selected therapeutic cells into a tissue at or near the site of tissue damage. Direct injection is accomplished using an intravascular catheter having a deployable needle, and injection is usually targeted into the adventitial and peri-adventitial tissues surrounding the blood vessel from which the needle is deployed.

24 Claims, 10 Drawing Sheets

(56) References Cited

OTHER PUBLICATIONS

Orlic et al., "Mobilized bone marrow cells repair the infracted heart, improving function and survival," *PNAS*, Aug. 28, 2001; 8(18):10344-10349.

Penn et al., "Autologous Cell transplantation for the treatment of damaged myocardium," *Progress in Cardiovascular Diseases*, Jul./Aug. 2002; 45(1): 21-32.

Shake et al, "Mesenchymal stem cell implantation in a swine myocardial infarct model: engraftment and functional effects". *Ann Thorac Surg* Jun. 2002; 73(6): 1919-25; discussion 1926.

Stamm et al., "Autologous bone-marrow stem-cell transplantation for myocardial regeneration," *Lancet*. Jan. 4, 2003;361(9351):45-46.

Strauer et al., "Repair of Infarcted Myocardium by Autologous Intracoronary Mononuclear Bone Marrow Cell Transplantation in Humans". *Circulation*. 2002;106:1913-1918.

Tomita et al.; "Improved heart function with myogenesis and angiogenesis after autologous porcine bone marrow stromal cell transplantation," *J Thorac Cardiovasc Surg* 2002;123:1132-1140.

Tse et al., "Angiogenesis in ischaemic myocardium by intramyocardial autologous bone marrow mononuclear cell implantation," *Lancet* 2003, 361: 47-49.

Yateishi-Yuyama et al. for the Therapeutic Angiogenesis using Cell Transplantation (TACT) Study Investigators; "Therapeutic angiogenesis for patients with limb ischaemia by autologous transplantation of bone-marrow cells: a pilot study and a randomized controlled trial," *Lancet* , 2002; 360: 427-35.

Yau et al., "Beneficial Effect of Autologous cell transplantation on infarcted heart function: comparison between bone marrow stromal cells and heart cells," *Ann Thorac Surg* 2003; 75: 169-77.

Zhong et al.; "Affects of different access routes on autologous satellite cell implantation stimulating myocardial regeneration," *Chin Med J (Engl)*. Oct. 2002;115(10):1521-1524.

Ly et al., "Transcoronary Delivery of Allogenic Bone Marrow-Derived Mesenchymal Stem Cells in a Swine Model of Recent Myocardial Infarction" American Heart Association, *AOS.503.01—Heart Failure: Cell- and Gene-Based Therapies II, Presentation Abstract 3698*, Nov. 17, 2009, Dallas, Texas.

\* cited by examiner

METHODS AND SYSTEMS FOR TREATING ISCHEMIC TISSUES

CROSS-REFERENCES TO RELATED APPLICATIONS

The present application is a continuation of U.S. patent application Ser. No. 10/829,905 filed Apr. 21, 2004 now abandoned, which claims priority of U.S. Patent Application Ser. No. 60/465,013, filed Apr. 22, 2003, the full disclosures of which are incorporated herein by reference.

BACKGROUND OF THE INVENTION

1. Field of the Invention

The present invention relates generally to medical methods and devices. More particularly, the present invention relates to methods and systems for treating ischemic cardiac and other tissue damaged by myocardial infarction and other causes by intravascularly injecting therapeutic cells at or near the damaged tissue.

Cardiac tissue can be damaged by a variety of causes, including myocardial infarction, cardiac tissue infections, diseases such as rheumatic fever, trauma, and the like. Extensive damage to myocardial or valve tissues can cause heart failure and death. Present treatments include heart transplantation, valve repair surgery, and drug therapies. None of these treatments, however, is effective for all patients, and heart failure remains a leading cause of death world wide.

Neurologic tissue can also become ischemic due to a number of causes, including blocked arteries, stroke, trauma, and the like.

Chronic limb ischemia is a condition that arises from the inability of diseased arteries to conduct sufficient blood flow to the lower leg, ankle and toes. It can cause persistent, recurring rest pain, ulceration and gangrene. If blood flow cannot be restored by surgical or interventional procedures, patients will eventually require amputation of the affected limb. Recently, a study reported positive results of autologous bone marrow cell transplantation into patients with limb ischemia due to peripheral artery disease.

Such cell therapy apparently provided re-vascularization by promoting development of collateral arteries flowing to the ischemic muscle. Cells were injected intramuscularly requiring the harvest of 500 ml of bone marrow. Such marrow harvest is very traumatic. If cells could be delivered more precisely to the affected muscles and placed in a non-ischemic depot where there viability was maintained, it should be possible to achieve patient benefit with fewer cells. This would reduce patient discomfort associated with the bone marrow procedure and improve dose response.

Much research is focused on developing therapies for inducing or enhancing the repair of damaged cardiac tissues in patients suffering from or at risk of heart failure. Some, such as transmyocardial revascularization, rely on inducing controlled injury to damaged heart tissue in the hope of causing revascularization and tissue regeneration. Other therapies intended to regenerate tissue include systemic and local administration of growth factors, angiogenic factors, and the like, to promote tissue repair.

Of particular interest to the present invention, the introduction of therapeutic cells into damaged cardiac tissues has been proposed. For example, the injection of pluripotent stem cells, such as embryonic stem cells or mesenchymal adult progenitor cells (MAPC's), has been shown to have therapeutic benefit when introduced into damaged cardiac tissues. Other cells and cell lines which are the subject of current research for cardiac tissue regeneration include cardiomyocytes, fibroblasts, endothelial cells, and skeletal myoblasts.

Despite this promise, the injection of therapeutic stem and other cells presents a number of challenges. Direct injection of the cells to the myocardium through an epicardial surface is difficult, requiring either an open chest or a transthoracic procedure. Open chest procedures are very traumatic, and transthoracic procedures are complicated and limit the ability to precisely locate the site into which the cells are to be injected.

Intracardiac protocols where the therapeutic cells are injected through the endocardial surface have also been proposed. Such inside-the-heart procedures are also complex and require sophisticated intracardial catheters with complicated positioning systems. Even with such advanced systems, the precise delivery of the therapeutic cells to a particular target location can be difficult.

A third alternative which has recently been proposed is to use an arterial infusion catheter to deliver cells within a blood vessel near the site of the damaged tissue. This catheter-based technique relies on blocking blood flow with a balloon and infusing cells distally into the artery. The need for the cells to migrate through the endothelium, however, may be problematic and ultimately limit the success of this approach. Recent studies have also shown that intraluminal delivery of cells results in micro-infarctions due to the extended balloon occlusion of the artery or the embolism of cellular material blocking capillary flow.

For these reasons, it would be desirable to provide improved methods and systems for delivering therapeutic cells to damaged coronary and other tissues. Such methods and systems will preferably be catheter-based and permit introduction of the cells into cardiac and other tissue via the coronary and peripheral vasculature, including both arteries and veins. The methods and systems should further provide for delivering the therapeutic cells to precisely controlled locations within or adjacent to the damaged tissues, and should also provide for direct delivery into the tissue without dilution in the systemic circulation. Preferably, the methods and systems will allow for injection of the therapeutic cells into the space between a blocked artery and an adjacent collateral vessel to promote enlargement of the collateral vessel. Additionally, the cells which are injected and those which proliferate in situ should be able to migrate and distribute from the site of injection into adjacent regions of damaged tissue in order to provide effective therapy. At least some of these objectives will be met by the inventions described hereinafter.

2. Description of the Background Art

The endocardial and epicardial injection of stem and other cells are described in U.S. Pat. Nos. 6,387,369; 6,099,832; 5,602,301; and 5,591,625, and U.S. Patent Publication No. US 2002/0182186. Isolation, purification and culturing of human mesenchymal stem cells are described in U.S. Pat. No. 5,486,359. The full disclosures of each of these patents and patent publication are incorporated herein by reference.

Publications of interest include:
1. Penn M S, Francis G S, Ellis S G, Young J B, McCarthy P M, Topol E J; "Autologous Cell Transplantation for the Treatment of Damaged Myocardium". Progress in Cardiovascular Diseases, Vol. 45, No. 1, July/August 2002: pp 21-32.
2. Assmus B, MD; Schachinger V, MD; Teupe C, MD; Britten M, MD; Lehmann R, MD; Dobert N, MD; Grunwald F, MD; Aicher A, MD; Urbich C, PhD; Martin H, MD; Hoelzer D, MD; Dimmeler S, PhD; Zeiher A M, MD; "Transplantation of Progenitor Cells and Regeneration Enhancement in Acute Myocardial Infarction (TOPCARE-AMI)". Circulation. 2002; 106: 3009-3017.
3. Stamm C, Westphal B, Kleine H-D, Petzsch M, Kittner C, Klinge H, Schumichen C, Nienaber C A, Freund M, Steinhoff G; "Autologous bone-marrow stem-cell transplantation for myocardial regeneration". The Lancet Vol. 361 Jan. 4, 2003.
4. Zhong H, Zhu H, Zhang Z; "Affects of different access routes on autologous satellite cell implantation stimulating myocardial regeneration". Chin Med J (Engl) 2002 October; 115(10): 1521-4.
5. Strauer B E, MD; Brehm M, MD; Zeus T, MD; Kostering M, MD; Hernandez A, PhD; Sorg R V, PhD; Kogler G, PhD; Wernet P, MD; "Repair of Infarcted Myocardium by Autologous Intracoronary Mononuclear Bone Marrow Cell Transplantation in Humans". Circulation. 2002; 106: 1913-1918.
6. Tse H-F, Kwong Y-L, Chan J K F, Lo G, Ho C-L, Lau C-P; "Angiogenesis in ischaemic myocardium by intramyocardial autologous bone marrow mononuclear cell implantation". The Lancet 2003; 361: 47-49.
7. Hagege A A, Carrion C, Menasche P, Vilquin J-T, Duboc D, Marolleau J-P, Desnos M, Bruneval P; "Viability and differentiation of autologous skeletal myoblast grafts in ischaemic cardiomyopathy". The Lancet 2003; 361: 91-92.
8. Yateishi-Yuyama E, Matsubara H, Murohara T, Ikeda U, Shintani S, Masaki H, Amano K, Kishimoto Y, Yoshimoto K, Akashi H, Shimada K, Iwasaka T, Imaizumi T for the Therapeutic Angiogenesis using Cell Transplantation (TACT) Study Investigators; "Therapeutic angiogenesis for patients with limb ischaemia by autologous transplantation of bone-marrow cells: a pilot study and a randomized controlled trial". The Lancet 2002; 360: 427-35.
9. Kawamoto A, MD; Tkebuchava T, MD; Yamaguchi J-I, MD; Nishimura H, MD; Yoon Y-S, MD; Milliken C, BS; Uchida S, MD; Masuo O, MD; Iwaguro H, MD; Ma H, BS; Hanley A, BS; Silver M, BS; Kearney M, BS; Losordo D W, MD; Isner J M, MD; Asahara T, MD; "Intramyocardial Transplantation of Autologous Endothelial Progenitor Cells for Therapeutic Neovascularization of Myocardial Ischemia". Circulation. 2003; 107: 461-468.
10. Min J. Y., Sullivan M F, Yang Y, Zhang J P, Converso K L, Morgan J P, Xia Y F; "Significant improvement of heart function by cotransplantation of human mesenchymal stem cells and fetal cardiomyocytes in postinfarcted pigs". Ann Thorac Surg 2002 November; 74(5): 1568-75.
11. Shake J G, Gruber P J, Baumgartner W A, Senechal G, Meyers J, Redmond J M, Pittenger M F, Martin B J; "Mesenchymal stem cell implantation in a swine myocardial infarct model: engraftment and functional effects". Ann Thorac Surg 2002 June; 73(6): 1919-25; discussion 1926.
12. Fuchs S, M D; Baffour R, PhD; Zhou Y F, MD; Shou M, MD; Pierre A, BSc; Tio F O, MD; Weissman N J, MD; Leon M B, MD; Epstein S E, MD; Kornowski R, MD; "Transendocardial Delivery of Autologous Bone Marrow Enhances Collateral Perfusion and Regional Function in Pigs With Chronic Experimental Myocardial Ischemia". Journal of the American College of Cardiology 2001; Vol. 37, No. 6: 1726-1732.
13. Tomita S, MD, PhD; Mickle D A G, MD; Weisel RD, MD; Jia Z-Q, MD; Tumiati L C, BSc; Allidina Y, RTNM; Liu P, MD; Li R-K, MD, PhD; "Improved heart function with myogenesis and angiogenesis after autologous porcine bone marrow stromal cell transplantation". Journal of Thoracic and Cardiovascular Surgery; June 2002: 1132-1140.
14. Li R-K, MD, PhD; Weisel R D, MD; Mickle D A G, MD; Jia Z-Q, MD; Kim E-J, MD; Sakai T, MD; Tomita S, MD; Schwartz L, MD; Iwanochko M, MD; Husain M, MD; Cusimano R J, MD, MSc; Burns R J, MD; Yau T M, M D, MSc; "Autologous Porcine Heart Cell Transplantation Improved Heart Function After A Myocardial Infarction". Journal of Thoracic and Cardiovascular Surgery; January 2000: 62-68.
15. Yau T M, MD, MS; Tomita S, MD; Weisel R D, MD; Jia Z-Q, MD; Tumiati L C, MS; Mickle D A G, MD; Li R-K, MD, PhD; "Beneficial Effect of Autologous Cell Transplantation on Infarcted Heart Function: Comparison Between Bone Marrow Stromal Cells and Heart Cells". Ann Thorac Surg 2003; 75: 169-77.
16. Orlic D, Kajstura J, Chinenti S, Jakoniuk I, Anderson S M, Li B, Pickel J, McKay R, Nadal-Ginard B, Bodine D M, Leri A, Anversa P; "Bone marrow cells regenerate infracted myocardium". Nature 2001 Apr. 5; 410 (6829): 701-5.
17. Orlic D, Kajstura J, Chimenti S, Limana F, Jakoniuk I, Quaini F, Nadal-Ginard B, Bodine D M, Leri A, Anversa P; "Mobilized bone marrow cells repair the infracted heart, improving function and survival". PNAS Aug. 28, 2001.
18. Kocher A A, Schuster M D, Szabolcs M J, Takuma S, Burkhoff D, Wang J, Homma S, Edwards N M, Itescu S; "Neovascularization of ischemic myocardium by human bone-marrow-derived angioblasts prevents cardiomyocyte apoptosis, reduces remodeling and improves cardiac function". Nature Medicine; Vol. 1, No. 4, April 2001: 430-36.
19. Jackson K A, Majka S M, Wang H, Pocius J, Hartley C J, Majesky M W, Entman M L, Michael L H, Hirschi K K, Goodell M A; "Regeneration of ischemic cardiac muscle and vascular endothelium by adult stem cells". Journal of Clinical Investigation, June 2001, Vol. 107, Number 11: 1395-1402.
20. Kawamoto A, MD; Gwon H-C, MD; Iwaguro H, MD; Yamaguchi J-I, MD; Uchida S, MD; Masuda H, MD; Silver M, BS; Ma H, BS; Kearney M, BS; Isner J M, MD; Asahara T, MD; "Therapeutic Potential of Ex Vivo Expanded Endothelial Progenitor Cells for Myocardial Ischemia". Circulation. 2001; 103: 634-637.

BRIEF SUMMARY OF THE INVENTION

The present invention provides improved methods and systems for treating patients at risk of or suffering from conditions related to ischemic and other damaged tissue, particularly from congestive heart failure, myocardial infarction, stroke, peripheral vascular disease, and other conditions of compromised circulation. The methods and systems of the present invention provide for the direct and local delivery of therapeutic cells at or near the location(s), typically ischemic cardiac or other tissue damage. Such direct and local administration is achieved using a catheter or other intravascular access device which is capable of injecting or otherwise introducing the therapeutic cells through the endothelium of an artery or vein into the target site within the cardiac and other tissue within or adjacent to the location of the damaged tissue to be treated. The therapeutic cells are thus delivered into the perivascular space, preferably within the adventitial regions where the cells may find a particularly conducive location for growth and proliferation. A presently preferred location is into a space in tissue between a blocked artery and an adjacent collateral vessel. By introducing the therapeutic cells at a location midway down the length of the blocked artery, enlargement of a nearby segment of a collateral blood vessel is achieved. Shear stress of arterial flow in the collateral vessel will then cause enlargement of the entire collateral vessel to revascularize the ischemic tissue. Moreover, it is believed that the cells may rapidly migrate from the adventia into the damaged regions of the myocardium or other target tissue where they will promote tissue regeneration and repair.

Suitable therapeutic cells include any known or presently unknown human or animal cell or cell line which can provide a therapeutic benefit when introduced into the perivascular or adventitial regions according to the methods described herein. Exemplary cells and cell lines include both autologous and heterologous cells, including stem cells, cardiomyocytes, fibroblasts, endothelial cells, skeletal myoblasts, and the like. Preferred are pluripotent stem cells, particularly mesenchymal adult progenitor cells, embryonic stem cells and mobilized peripheral blood stem cells. Efficient periadventitial or perivascular injection will allow use of autologous bone marrow and/or mobilized peripheral blood stem cells with little or no enrichment, isolation, or manipulation.

The methods and systems of the present invention rely on injection of the therapeutic stem cells into the adventitial or perivascular tissue surrounding the impaired blood vessels in the coronary and peripheral vasculature. Delivery of the therapeutic cells into these ischemic tissues results in rapid migration and distribution of the cells throughout the adventitial pericardial space and into the myocardium, particularly to regions of the myocardium which are damaged and in need of regeneration. Optionally, injection of the therapeutic cells may be made at multiple sites and/or at different times in order to further enhance even and rapid distribution and persistence of the therapeutic cells over wide regions and/or prolonged periods.

Preferably, injecting the therapeutic cells into the adventitial and perivascular tissues comprises advancing a needle from a lumen of the blood vessel to the location beyond the endothelium. The therapeutic cells are then delivered through the needle to the target tissues. Typically, the needle is advanced into a perivascular space beyond the outside of the endothelium of the blood vessel, more typically being advanced into the adventitia surrounding the blood vessel. The needle may be advanced in a radial direction to a depth in the adventitia equal to at least 10% of the mean luminal diameter of the blood vessel at the site of injection. More typically being in the range from 10% to 50% of the mean luminal diameter.

Systems according to the present invention for damaged cardiac tissues comprise an amount of therapeutic cells selected to treat the tissue damage and an intravascular catheter having a needle for injecting the substance into a location beyond the endothelium of the blood vessel.

DETAILED DESCRIPTION OF THE INVENTION

The present invention provides methods and systems for treating patients at risk of or suffering conditions associated with damaged or ischemic tissue. In particular, these patients will have been diagnosed to have region(s) of damaged tissues such as ischemic tissues, particularly ischemic cardiac tissue, neurologic tissue, and tissue in the legs at risk of peripheral vascular disease by conventional techniques. Ischemic cardiac tissue may be located by angiogram, while compromised circulation in the peripheral vasculature can be identified by other conventional techniques.

The present invention will preferably utilize microfabricated devices and methods for intravascular injection of the therapeutic cells. The following description provides several representative embodiments of microfabricated needles (microneedles) and macroneedles suitable for the delivery of the therapeutic cells into a perivascular space or adventitial tissue. The perivascular space is the potential space between the outer surface and the endothelium or "vascular wall" of either an artery or vein. The microneedle is usually inserted substantially normal to the wall of a vessel (artery or vein) to eliminate as much trauma to the patient as possible. Until the microneedle is at the site of an injection, it is positioned out of the way so that it does not scrape against arterial or venous walls with its tip. Specifically, the microneedle remains enclosed in the walls of an actuator or sheath attached to a catheter so that it will not injure the patient during intervention or the physician during handling. When the injection site is reached, movement of the actuator along the vessel is terminated, and the actuator is operated to cause the microneedle to be thrust outwardly, substantially perpendicular to the central axis of a vessel, for instance, in which the catheter has been inserted.

Figure 1A:
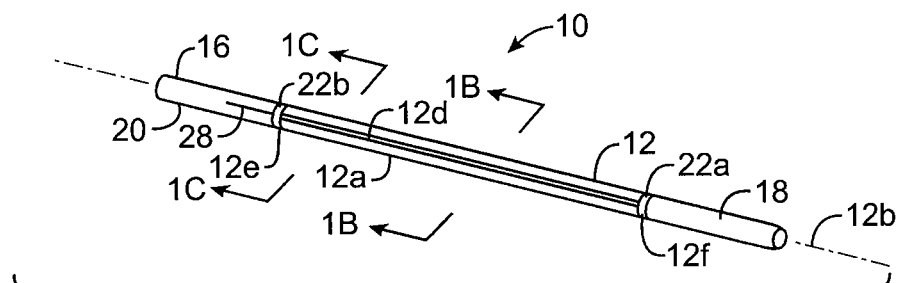
FIG. 1A is a schematic, perspective view of an intravascular injection catheter suitable for use in the methods and systems of the present invention.
Figure 1B:
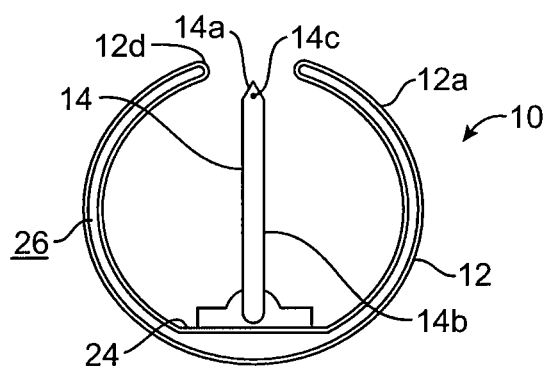
FIG. 1B is a cross-sectional view along line 1B-1B of FIG. 1A.
Figure 1C:
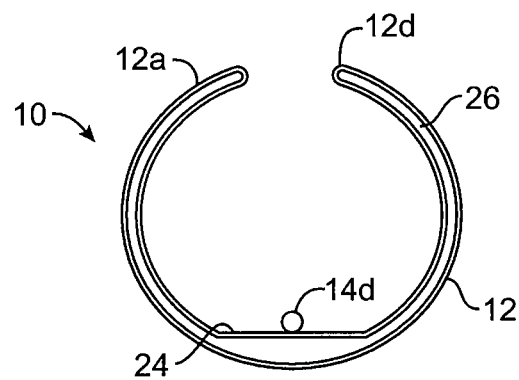
FIG. 1C is a cross-sectional view along line 1C-1C of FIG. 1A.
Figure 2A:
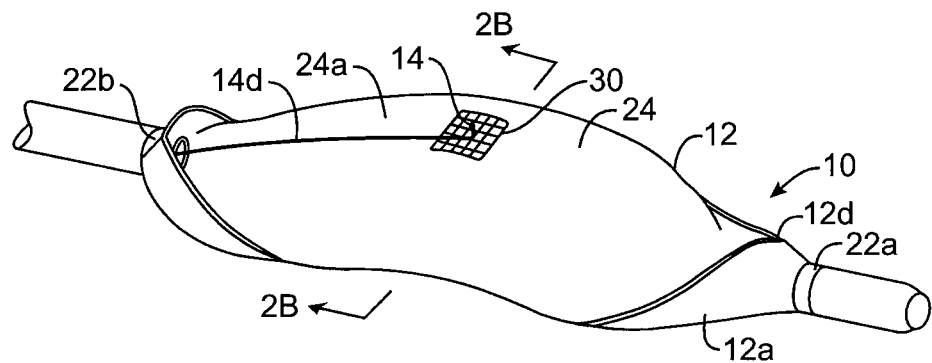
FIG. 2A is a schematic, perspective view of the catheter of FIGS. 1A-1C shown with the injection needle deployed.
Figure 2B:
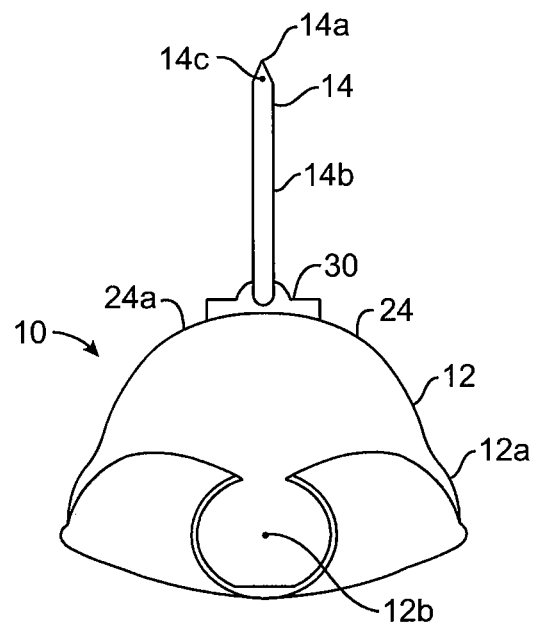
FIG. 2B is a cross-sectional view along line 2B-2B of FIG. 2A.

As shown in FIGS. 1A-2B, a microfabricated intravascular catheter 10 includes an actuator 12 having an actuator body 12a and central longitudinal axis 12 b. The actuator body more or less forms a C-shaped outline having an opening or slit 12d extending substantially along its length. A microneedle 14 is located within the actuator body, as discussed in more detail below, when the actuator is in its unactuated condition (furled state) (FIG. 1B). The microneedle is moved outside the actuator body when the actuator is operated to be in its actuated condition (unfurled state) (FIG. 2B).

The actuator may be capped at its proximal end 12e and distal end 12f by a lead end 16 and a tip end 18, respectively, of a therapeutic catheter 20. The catheter tip end serves as a means of locating the actuator inside a blood vessel by use of a radio opaque coatings or markers. The catheter tip also forms a seal at the distal end 12f of the actuator. The lead end of the catheter provides the necessary interconnects (fluidic, mechanical, electrical or optical) at the proximal end 12e of the actuator.

Retaining rings 22a and 22b are located at the distal and proximal ends, respectively, of the actuator. The catheter tip is joined to the retaining ring 22a, while the catheter lead is joined to retaining ring 22b. The retaining rings are made of a thin, on the order of 10 to 100 microns (μm), substantially rigid material, such as Parylene (types C, D or N), or a metal, for example, aluminum, stainless steel, gold, titanium or tungsten. The retaining rings form a rigid substantially "C"-shaped structure at each end of the actuator. The catheter may be joined to the retaining rings by, for example, a butt-weld, an ultra sonic weld, integral polymer encapsulation or an adhesive such as an epoxy.

The actuator body further comprises a central, expandable section 24 located between retaining rings 22a and 22b. The expandable section 24 includes an interior open area 26 for rapid expansion when an activating fluid is supplied to that area. The central section 24 is made of a thin, semi-rigid or rigid, expandable material, such as a polymer, for instance, Parylene (types C, D or N), silicone, polyurethane or polyimide. The central section 24, upon actuation, is expandable somewhat like a balloon-device.

The central section is capable of withstanding pressures of up to about 100 psi upon application of the activating fluid to the open area 26. The material from which the central section is made of is rigid or semi-rigid in that the central section returns substantially to its original configuration and orientation (the unactuated condition) when the activating fluid is removed from the open area 26. Thus, in this sense, the central section is very much unlike a balloon which has no inherently stable structure.

The open area 26 of the actuator is connected to a delivery conduit, tube or fluid pathway 28 that extends from the catheter's lead end to the actuator's proximal end. The activating fluid is supplied to the open area via the delivery tube. The delivery tube may be constructed of Teflon© or other inert plastics. The activating fluid may be a saline solution or a radio-opaque dye.

The microneedle 14 may be located approximately in the middle of the central section 24. However, as discussed below, this is not necessary, especially when multiple microneedles are used. The microneedle is affixed to an exterior surface 24a of the central section. The microneedle is affixed to the surface 24a by an adhesive, such as cyanoacrylate. Alternatively, the microneedle maybe joined to the surface 24a by a metallic or polymer mesh-like structure 30 (See FIG. 4F), which is itself affixed to the surface 24a by an adhesive. The mesh-like structure may be-made of, for instance, steel or nylon.

The microneedle includes a sharp tip 14a and a shaft 14b. The microneedle tip can provide an insertion edge or point. The shaft 14b can be hollow and the tip can have an outlet port 14c, permitting the injection of a pharmaceutical or drug into a patient. The microneedle, however, does not need to be hollow, as it may be configured like a neural probe to accomplish other tasks.

As shown, the microneedle extends approximately perpendicularly from surface 24a. Thus, as described, the microneedle will move substantially perpendicularly to an axis of a vessel or artery into which has been inserted, to allow direct puncture or breach of vascular walls.

The microneedle further includes a pharmaceutical or drug supply conduit, tube or fluid pathway 14d which places the microneedle in fluid communication with the appropriate fluid interconnect at the catheter lead end. This supply tube may be formed integrally with the shaft 14b, or it may be formed as a separate piece that is later joined to the shaft by, for example, an adhesive such as an epoxy.

The needle 14 may be a 30-gauge, or smaller, steel needle. Alternatively, the microneedle may be microfabricated from polymers, other metals, metal alloys or semiconductor materials. The needle, for example, may be made of Parylene, silicon or glass. Microneedles and methods of fabrication are described in U.S. application Ser. No. 09/877,653, filed Jun. 8, 2001, entitled "Microfabricated Surgical Device", having a common inventor with the subject application, the entire disclosure of which is incorporated herein by reference.

Figure 3:
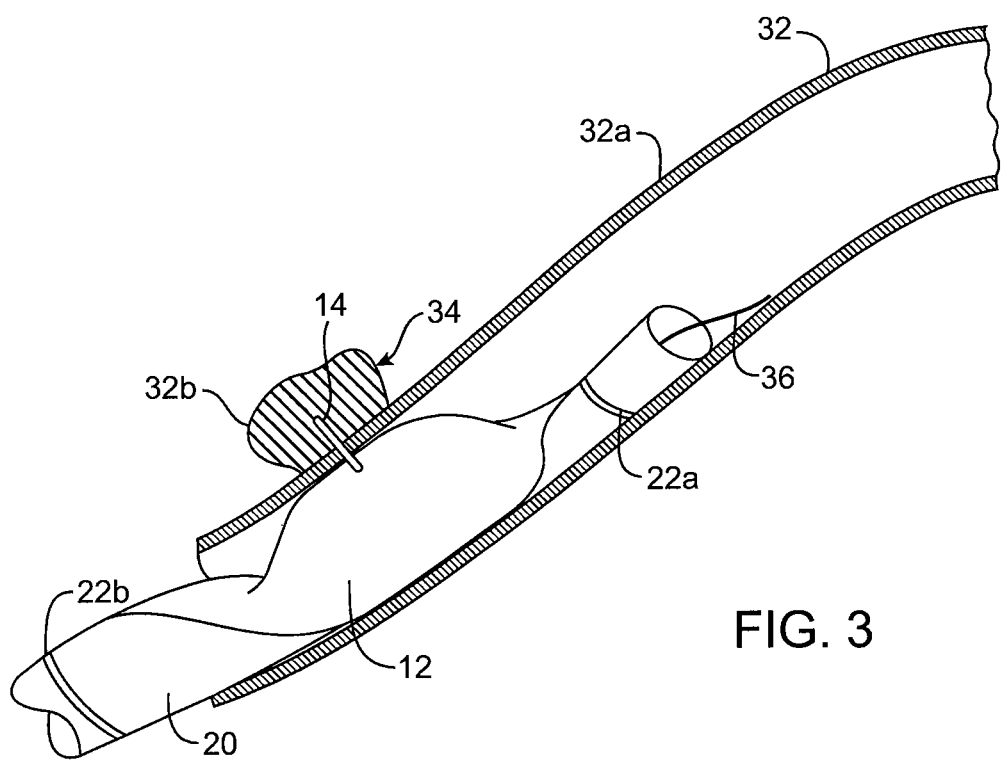
FIG. 3 is a schematic, perspective view of the intravascular catheter of FIGS. 1A-1C injecting therapeutic cells into an adventitial space surrounding a coronary blood vessel in accordance with the methods of the present invention.

The catheter 20, in use, is inserted through an artery or vein and moved within a patient's vasculature, for instance, a vein 32, until a specific, targeted region 34 is reaches (see FIG. 3). The targeted region 34 may be the site of tissue damage or more usually will be adjacent the sites typically being within 100 mm or less to allow migration of the cells. As is well known in catheter-based interventional procedures, the catheter 20 may follow a guide wire 36 that has previously been inserted into the patient. Optionally, the catheter 20 may also follow the path of a previously-inserted guide catheter (not shown) that encompasses the guide wire.

During maneuvering of the catheter 20, well-known methods of fluoroscopy or magnetic resonance imaging (MRI) can be used to image the catheter and assist in positioning the actuator 12 and the microneedle 14 at the target region. As the catheter is guided inside the patient's body, the microneedle remains furled or held inside the actuator body so that no trauma is caused to the vascular walls.

After being positioned at the target region 34, movement of the catheter is terminated and the activating fluid is supplied to the open area 26 of the actuator, causing the expandable section 24 to rapidly unfurl, moving the microneedle 14 in a substantially perpendicular direction, relative to the longitudinal central axis 12b of the actuator body 12a, to puncture a vascular wall 32a. It may take only between approximately 100 milliseconds and two seconds for the microneedle to move from its furled state to its unfurled state.

The ends of the actuator at the retaining rings 22a and 22b remain rigidly fixed to the catheter 20. Thus, they do not deform during actuation. Since the actuator begins as a furled structure, its so-called pregnant shape exists as an unstable buckling mode. This instability, upon actuation, produces a large-scale motion of the microneedle approximately perpendicular to the central axis of the actuator body, causing a rapid puncture of the vascular wall without a large momentum transfer. As a result, a microscale opening is produced with very minimal damage to the surrounding tissue. Also, since the momentum transfer is relatively small, only a negligible bias force is required to hold the catheter and actuator in place during actuation and puncture.

The microneedle, in fact, travels so quickly and with such force that it can enter perivascular tissue 32b as well as vascular tissue. Additionally, since the actuator is "parked" or stopped prior to actuation, more precise placement and control over penetration of the vascular wall are obtained.

After actuation of the microneedle and delivery of the cells to the target region via the microneedle, the activating fluid is exhausted from the open area 26 of the actuator, causing the expandable section 24 to return to its original, furled state. This also causes the microneedle to be withdrawn from the vascular wall. The microneedle, being withdrawn, is once again sheathed by the actuator.

Various microfabricated devices can be integrated into the needle, actuator and catheter for metering flows, capturing samples of biological tissue, and measuring pH. The device 10, for instance, could include electrical sensors for measuring the flow through the microneedle as well as the pH of the pharmaceutical being deployed. The device 10 could also include an intravascular ultrasonic sensor (IVUS) for locating vessel walls, and fiber optics, as is well known in the art, for viewing the target region. For such complete systems, high integrity electrical, mechanical and fluid connections are provided to transfer power, energy, and pharmaceuticals or biological agents with reliability.

By way of example, the microneedle may have an overall length of between about 200 and 3,000 microns (μm). The interior cross-sectional dimension of the shaft 14b and supply tube 14d may be on the order of 20 to 250 um, while the tube's and shaft's exterior cross-sectional dimension may be between about 100 and 500 μm. The overall length of the actuator body may be between about 5 and 50 millimeters (mm), while the exterior and interior cross-sectional dimensions of the actuator body can be between about 0.4 and 4 mm, and 0.5 and 5 mm, respectively. The gap or slit through which the central section of the actuator unfurls may have a length of about 4-40 mm, and a cross-sectional dimension of about 50-500 μm. The diameter of the delivery tube for the activating fluid may be about 100 μm. The catheter size may be between 1.5 and 15 French (Fr).

Variations of the invention include a multiple-buckling actuator with a single supply tube for the activating fluid. The multiple-buckling actuator includes multiple needles that can be inserted into or through a vessel wall for providing injection at different locations or times.

Figure 4:
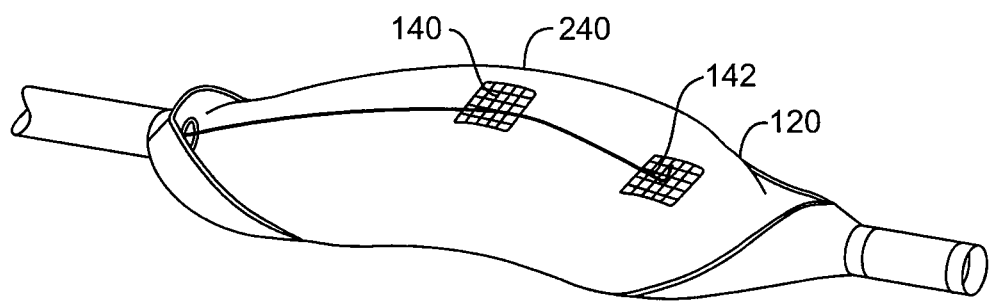
FIG. 4 is a schematic, perspective view of another embodiment of an intravascular injection catheter useful in the methods of the present invention.

For instance, as shown in FIG. 4, the actuator 120 includes microneedles 140 and 142 located at different points along a length or longitudinal dimension of the central, expandable section 240. The operating pressure of the activating fluid is selected so that the microneedles move at the same time. Alternatively, the pressure of the activating fluid may be selected so that the microneedle 140 moves before the microneedle 142.

Specifically, the microneedle 140 is located at a portion of the expandable section 240 (lower activation pressure) that, for the same activating fluid pressure, will buckle outwardly before that portion of the expandable section (higher activation pressure) where the microneedle 142 is located. Thus, for example, if the operating pressure of the activating fluid within the open area of the expandable section 240 is two pounds per square inch (psi), the microneedle 140 will move before the microneedle 142. It is only when the operating pressure is increased to four psi, for instance, that the microneedle 142 will move. Thus, this mode of operation provides staged buckling with the microneedle 140 moving at time $t_1$, and pressure $p_1$, and the microneedle 142 moving at time $t_2$ and $p_2$, with $t_1$, and $p_1$, being less than $t_2$ and $p_2$, respectively.

This sort of staged buckling can also be provided with different pneumatic or hydraulic connections at different parts of the central section 240 in which each part includes an individual microneedle.

Figure 5:
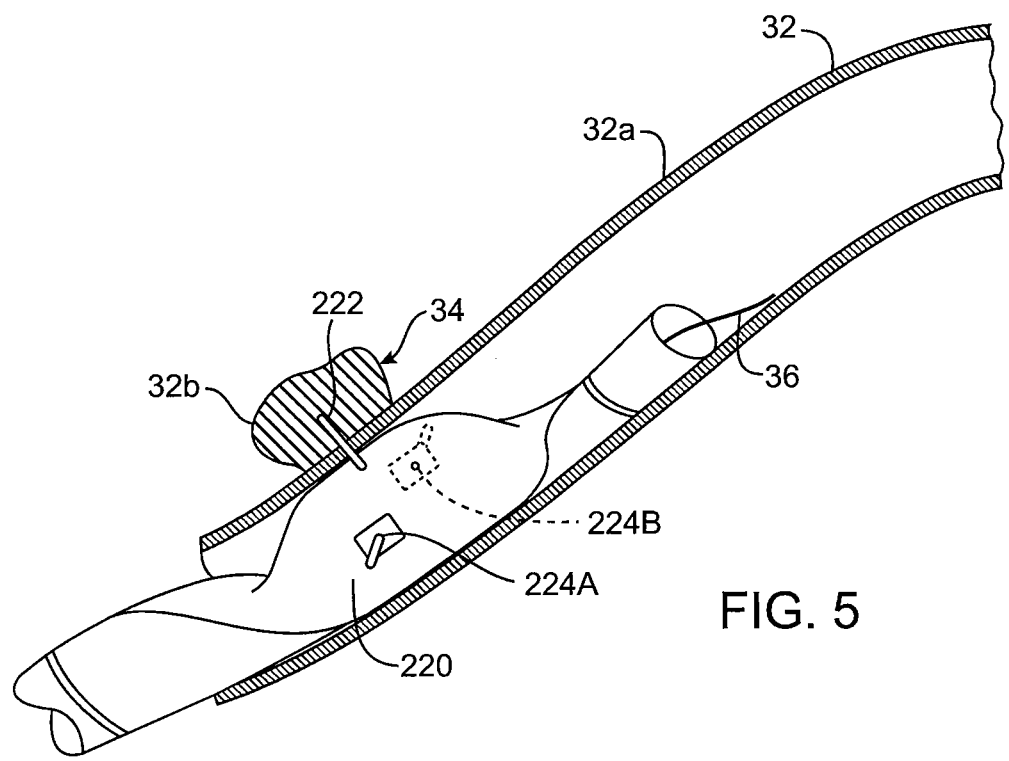
FIG. 5 is a schematic, perspective view of still another embodiment of an intravascular injection catheter useful in the methods of the present invention, as inserted into a patient's vasculature.

Also, as shown in FIG. 5, an actuator 220 could be constructed such that its needles 222 and 224A move in different directions. As shown, upon actuation, the needles move at angle of approximately 90° to each other to puncture different parts of a vessel wall. A needle 224B (as shown in phantom) could alternatively be arranged to move at angle of about 180° to the needle 224A.

Figure 6A:
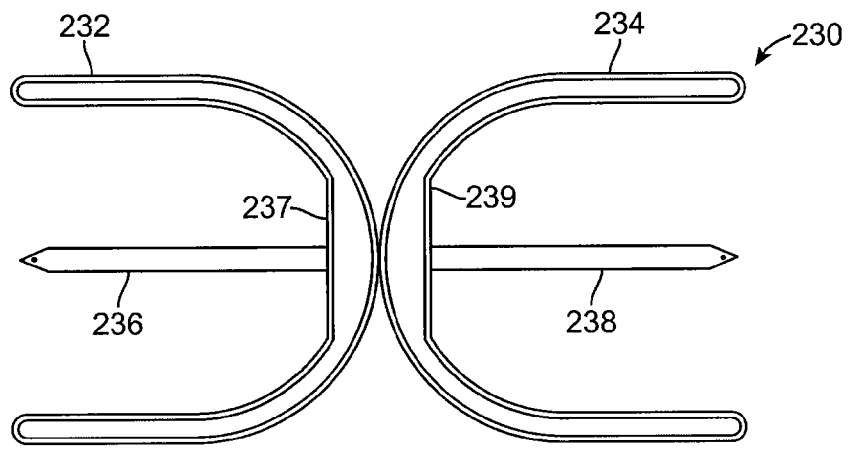
FIGS. 6A and 6B are schematic views of other embodiments of an intravascular injection catheter useful in the methods of the present invention (in an unactuated condition) including multiple needles.
Figure 6B:
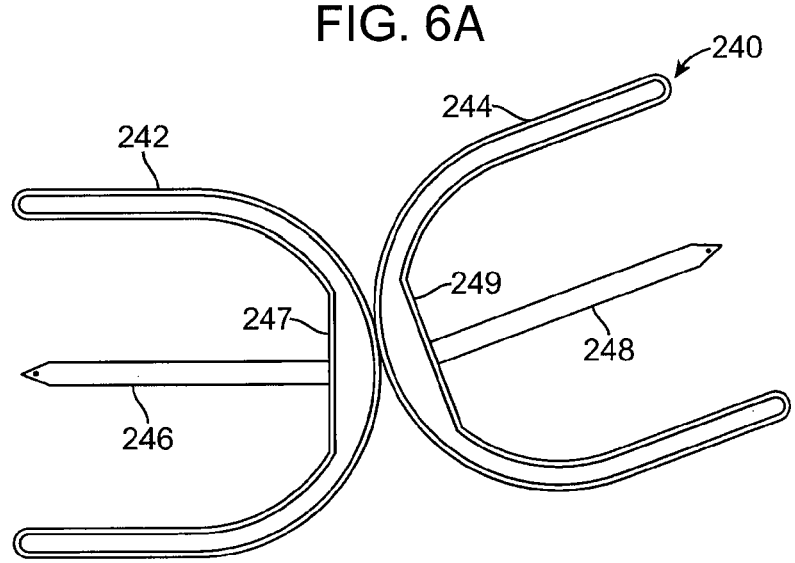

Moreover, as shown in FIG. 6A, in another embodiment, an actuator 230 comprises actuator bodies 232 and 234 including needles 236 and 238, respectively, that move approximately horizontally at an angle of about 180° to each other. Also, as shown in FIG. 7B, an actuator 240 comprises actuator bodies 242 and 244 including needles 242 and 244, respectively, that are configured to move at some angle relative to each other than 90° or 180°. The central expandable section of the actuator 230 is provided by central expandable sections 237 and 239 of the actuator bodies 232 and 234, respectively. Similarly, the central expandable section of the actuator 240 is provided by central expandable sections 247 and 249 of the actuator bodies 242 and 244, respectively.

Figure 7:
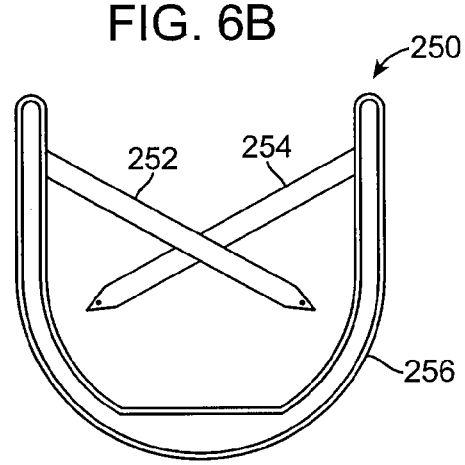
FIG. 7 is a schematic view of yet another embodiment of an intravascular injection catheter useful in the methods of the present invention (in an unactuated condition).

Additionally, as shown in FIG. 7, an actuator 250 may be constructed that includes multiple needles 252 and 254 that move in different directions when the actuator is caused to change from the unactuated to the actuated condition. The needles 252 and 254, upon activation, do not move in a substantially perpendicular direction relative to the longitudinal axis of the actuator body 256.

The above catheter designs and variations thereon, are described in published U.S. Patent Application Nos. 2003/005546 and 2003/0055400, the full disclosures of which are incorporated herein by reference. Co-pending application Ser. No. 10/350,314, assigned to the assignee of the present application, describes the ability of substances delivered by direct injection into the adventitial and pericardial tissues of the heart to rapidly and evenly distribute within the heart tissues, even to locations remote from the site of injection. The full disclosure of that co-pending application is also incorporated herein by reference. An alternative needle catheter design suitable for delivering the therapeutic cells of the present invention will be described below. That particular catheter design is described and claimed in co-pending application Ser. No. 10/397,700, filed on Mar. 19, 2003, the full disclosure of which is incorporated herein by reference.

Figure 8:
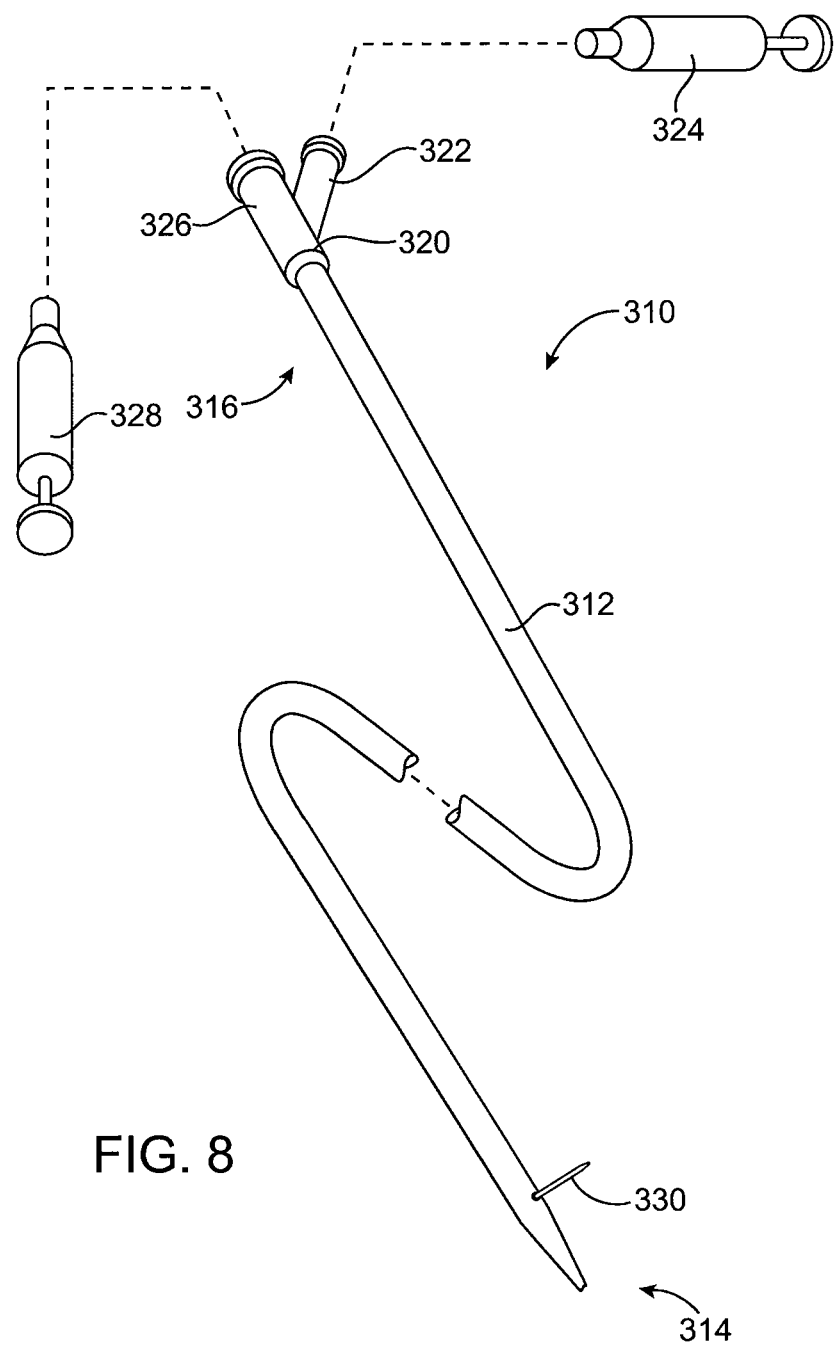
FIG. 8 is a perspective view of a needle injection catheter useful in the methods and systems of the present invention.

Referring now to FIG. 8, a needle injection catheter 310 constructed in accordance with the principles of the present invention comprises a catheter body 312 having a distal end 314 and a proximal 316. Usually, a guide wire lumen 313 will be provided in a distal nose 352 of the catheter, although over-the-wire and embodiments which do not require guide wire placement will also be within the scope of the present invention. A two-port hub 320 is attached to the proximal end 316 of the catheter body 312 and includes a first port 322 for delivery of a hydraulic fluid, e.g., using a syringe 324, and a second port 326 for delivering the pharmaceutical agent, e.g., using a syringe 328. A reciprocatable, deflectable needle 330 is mounted near the distal end of the catheter body 312 and is shown in its laterally advanced configuration in FIG. 8.

Figure 9:
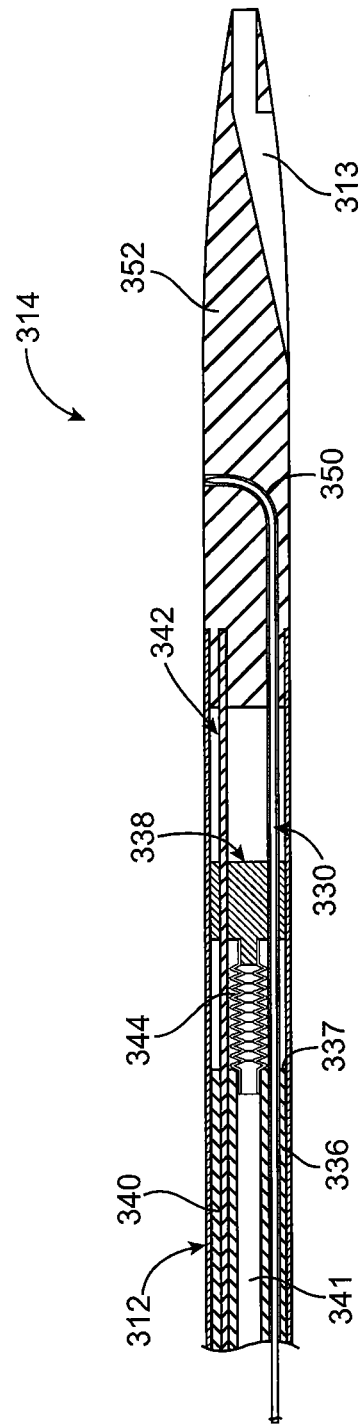
FIG. 9 is a cross-sectional view of the catheter FIG. 8 shown with the injection needle in a retracted configuration.

Referring now to FIG. 9, the proximal end 314 of the catheter body 312 has a main lumen 336 which holds the needle 330, a reciprocatable piston 338, and a hydraulic fluid delivery tube 340. The piston 338 is mounted to slide over a rail 342 and is fixedly attached to the needle 330. Thus, by delivering a pressurized hydraulic fluid through a lumen 341 tube 340 into a bellows structure 344, the piston 338 may be advanced axially toward the distal tip in order to cause the needle to pass through a deflection path 350 formed in a catheter nose 352.

Figure 10:
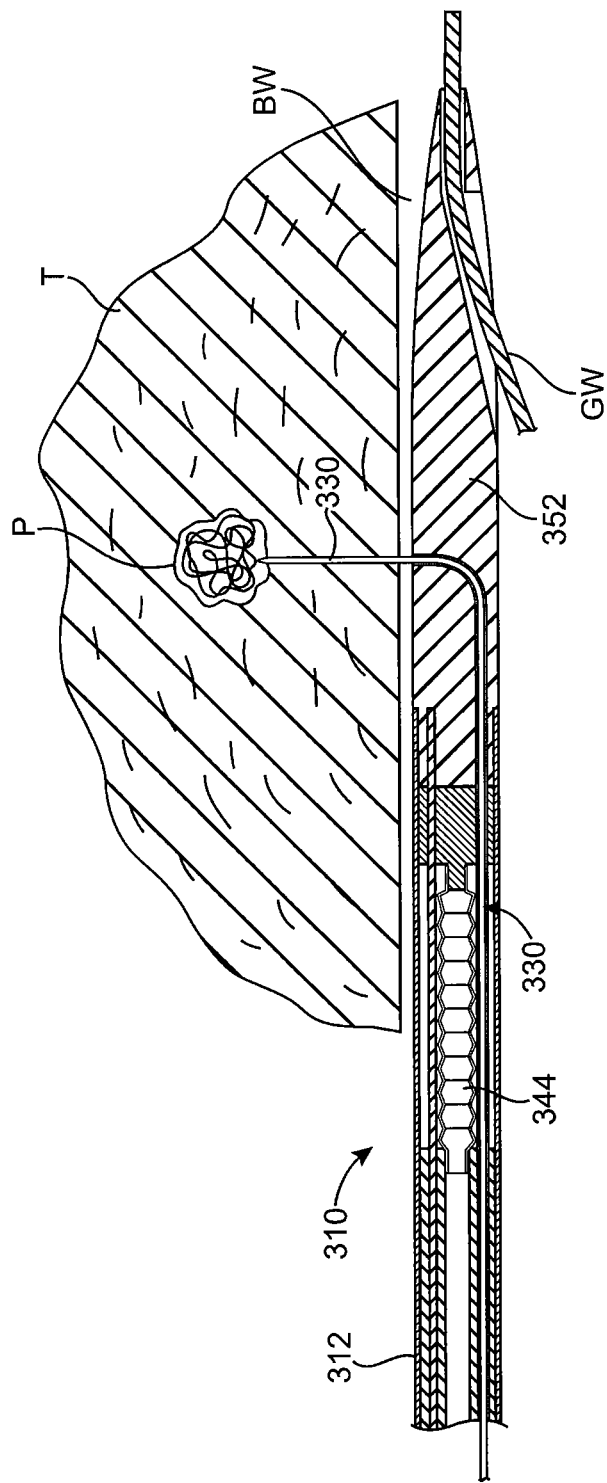
FIG. 10 is a cross-sectional view similar to FIG. 9, shown with the injection needle laterally advanced into luminal tissue for the delivery of therapeutic cells according to the present invention.

As can be seen in FIG. 10, the catheter 310 may be positioned in a coronary blood vessel BV, over a guide wire GW in a conventional manner. Distal advancement of the piston 338 causes the needle 330 to advance into luminal tissue T adjacent to the catheter when it is present in the blood vessel. The therapeutic cells may then be introduced through the port 326 using syringe 328 in order to introduce a plume P of agent in the cardiac tissue, as illustrated in FIG. 10. The plume P will be within or adjacent to the region of tissue damage as described above.

The needle 330 may extend the entire length of the catheter body 312 or, more usually, will extend only partially in therapeutic cells delivery lumen 337 in the tube 340. A proximal end of the needle can form a sliding seal with the lumen 337 to permit pressurized delivery of the agent through the needle.

The needle 330 will be composed of an elastic material, typically an elastic or super elastic metal, typically being nitinol or other super elastic metal. Alternatively, the needle 330 could be formed from a non-elastically deformable or malleable metal which is shaped as it passes through a deflection path. The use of non-elastically deformable metals, however, is less preferred since such metals will generally not retain their straightened configuration after they pass through the deflection path.

The bellows structure 344 may be made by depositing by parylene or another conformal polymer layer onto a mandrel and then dissolving the mandrel from within the polymer shell structure. Alternatively, the bellows 344 could be made from an elastomeric material to form a balloon structure. In a still further alternative, a spring structure can be utilized in, on, or over the bellows in order to drive the bellows to a closed position in the absence of pressurized hydraulic fluid therein.

After the therapeutic cells are delivered through the needle 330, as shown in FIG. 10, the needle is retracted and the catheter either repositioned for further agent delivery or withdrawn. In some embodiments, the needle will be retracted simply by aspirating the hydraulic fluid from the bellows 344. In other embodiments, needle retraction may be assisted by a return spring, e.g., locked between a distal face of the piston 338 and a proximal wall of the distal tip 352 (not shown) and/or by a pull wire attached to the piston and running through lumen 341.

EXPERIMENTAL

Figure 11:
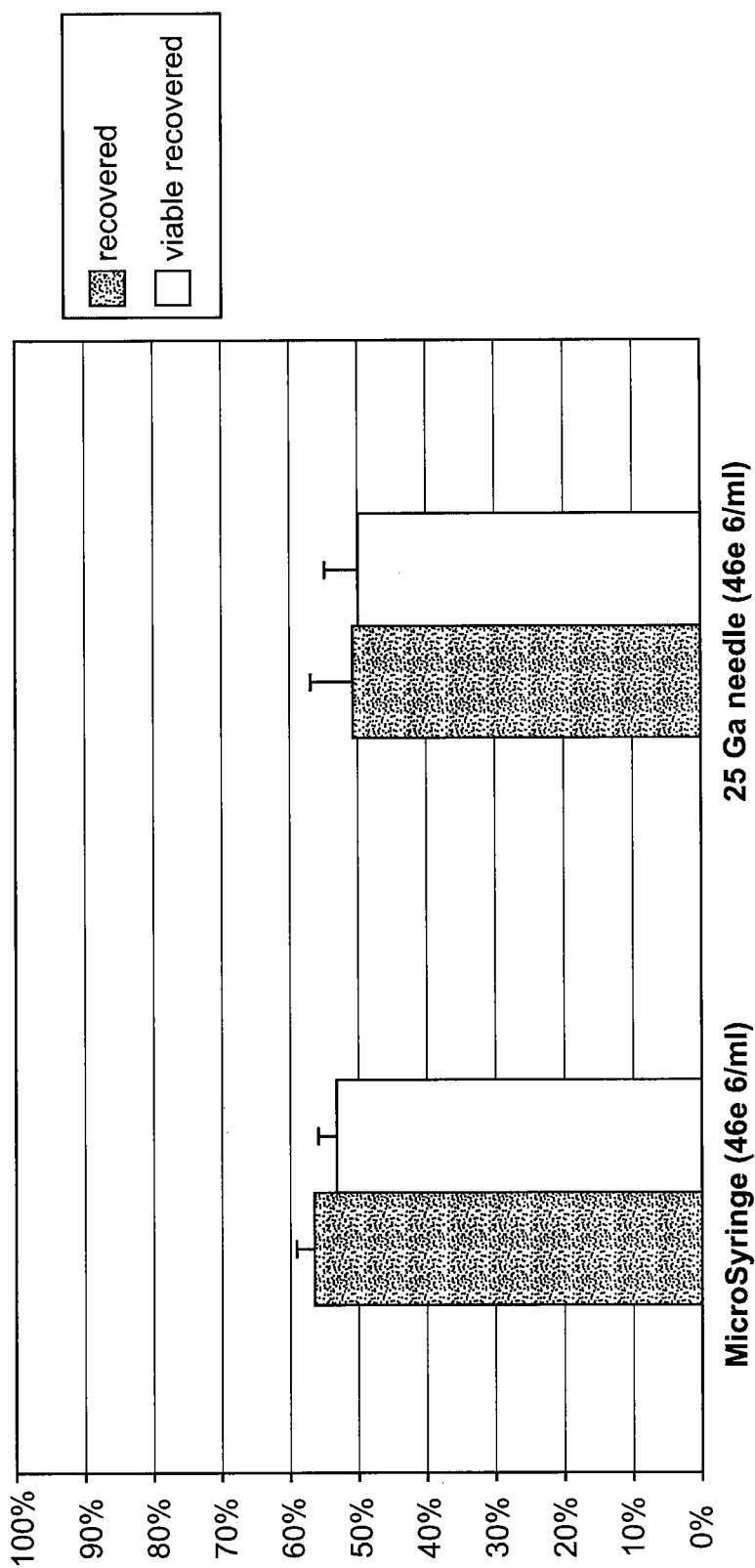
FIG. 11 is a chart comparing the viability of cells injected through a 25 G needle and through a microsyringe in accordance with the principles of the present invention.

Comparison of Cell Recovery/Viability after Passage Through the μSyringe Versus a 25 G Needle Methods. Porcine bone marrow cells were aseptically harvested from a needle-aspirate, washed in saline and centrifuged through Ficoll. Triplicate 500 μl aliquots (23×106 cells) of the resulting mononuclear cells (MNCs) were injected into tubes containing saline. Cell quantification and cell viability were determined before and after injection by propidium iodide/flow cytometry. Solid bars: % cells recovered; open bars: % viable cells recovered (FIG. 11).

Results. Injecting 500 ml post-Ficoll porcine bone marrow cells (46×106/ml) through the μSyringe or a tuberculin syringe (25 gauge needle) resulted in identical recovery and viability of cells in vitro.

Feasibility of Periadventitial Cell Delivery in Coronary Arteries

Figure 12B:
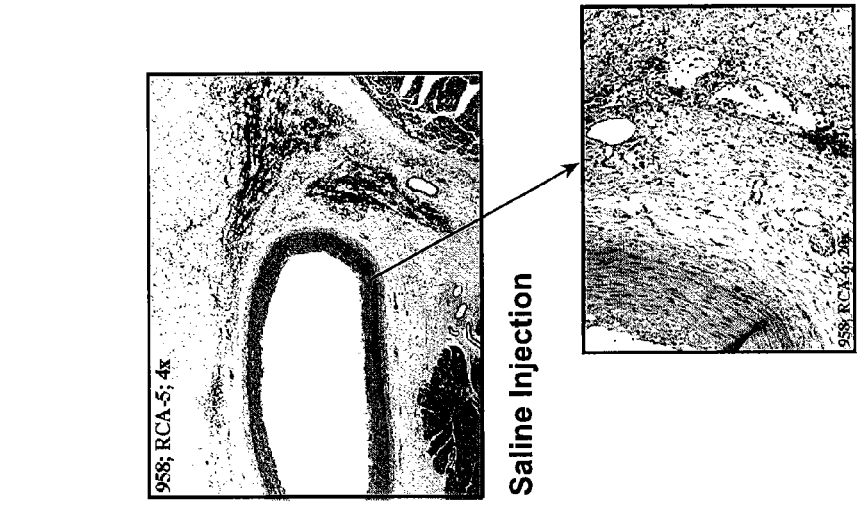
FIGS. 12A and 12B compare the formation of ectopic cell clusters in response to the injection of porcine mononuclear cells (FIG. 12A) and saline (FIG. 12B).
Figure 12A:
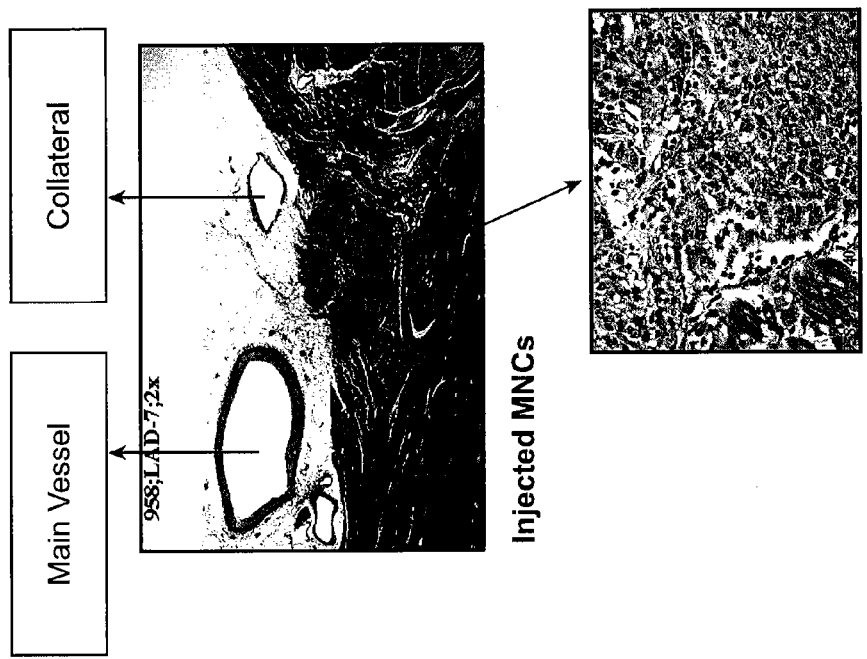

Methods. Porcine MNCs were harvested from peripheral blood with a B-D Vacutainer® CPT and washed in saline. Each of the coronary arteries received two 500 μl injections 3.4×10$^6$ cells, or 50:50 saline:contrast media spaced 1 cm apart. After sacrifice at 3 days, cardiac tissues near injection sites were H&E stained and prepared for histology. Photomicrography shows ectopic cell clusters in the peri-vascular space between the LAD and myocardium (FIG. 12A). In contrast, saline injection in the right coronary artery (RCA) resulted in diffuse RBCs and inflammatory infiltrates but no ectopic cell clusters (FIG. 12B).

Results. Injecting autologous MNCs into the adventitia of distal coronaries resulted in ectopic cell clusters (non-cardiomyocyte) within the underlying myocardium. Ectopic cell clusters persisted at 3 days after injecting into the left anterior descending artery. In contrast, saline injections resulted in diffuse RBC and inflammatory infiltrates in perivascular space but no ectopic cell clusters.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for treating ischemic cardiac tissue, said method comprising:
   injecting therapeutic cells through the endothelium of a coronary blood vessel into tissue at a location in the perivascular space surrounding the coronary blood vessel adjacent to the ischemic cardiac tissue and between the coronary blood vessel and myocardium to revascularize the ischemic cardiac tissue, wherein a needle is advanced beyond the external elastic lamina of the blood vessel to inject the therapeutic cells.

2. A method as in claim 1, wherein the coronary blood vessel is an artery.

3. A method as in claim 1, wherein the coronary blood vessel is a vein.

4. A method as in claim 1, wherein injecting comprises advancing the needle from a lumen of the coronary blood vessel to the location beyond the endothelium and infusing the therapeutic cells through the needle.

5. A method as in claim 1, wherein the ischemic cardiac tissue is cardiac tissue which has been damaged by a myocardial infarction or by inadequate blood circulation.

6. A method as in claim 1, wherein the therapeutic cells are selected from the group consisting of stem cells, cardiomyocytes, fibroblasts, endothelial cells, skeletal myoblasts, mesenchymal stem cells, cells from unprocessed or minimally processed bone marrow, peripheral blood stem cells, and mobilized peripheral blood stem cells.

7. A method as in claim 1, wherein the therapeutic cells are pluripotent stem cells.

8. A method as in claim 7, wherein the pluripotent stem cells are mesenchymal adult progenitor cells.

9. A method for treating damaged cardiac tissue, said method comprising:
   advancing a needle from a lumen of a coronary blood vessel adjacent the damaged cardiac tissue to a location beyond the external elastic lamina of the blood vessel and in the perivascular space surrounding the blood vessel and between the coronary blood vessel and myocardium; and
   injecting therapeutic cells through the needle into tissue at the location to revascularize the adjacent damaged cardiac tissue.

10. A method as in claim 9, wherein the coronary blood vessel is a coronary artery.

11. A method as in claim 9, wherein the coronary blood vessel is a coronary vein.

12. A method as in claim 9, wherein the needle is advanced beyond the external elastic lamina of the coronary blood vessel.

13. A method as in claim 10, wherein the needle is advanced in a radial direction to a depth beyond the endothelium equal to at least 10% of the mean luminal diameter of the coronary blood vessel at the needle location.

14. A method as in claim 13, wherein the depth is a distance in the range from 10% to 50% of the mean luminal diameter of the coronary blood vessel at the location.

15. A method as in claim 10, wherein the damaged coronary tissue has been damaged by a myocardial infarction.

16. A method as in claim 9, wherein the therapeutic cells are selected from the group consisting of stem cells, cardiomyocytes, fibroblasts, endothelial cells, skeletal myoblasts, mesenchymal stem cells, cells from unprocessed or minimally processed bone marrow, peripheral blood stem cells, and mobilized peripheral blood stem cells.

17. A method as in claim 15, wherein the therapeutic cells are pluripotent stem cells.

18. A method as in claim 15, wherein the pluripotent stem cells are mesenchymal adult progenitor cells.

19. A method for treating ischemic tissue, said method comprising:
    injecting therapeutic cells through the endothelium of a peripheral blood vessel into tissue at a location in the perivascular tissue surrounding the peripheral blood vessel adjacent to the ischemic tissue to revascularize the ischemic tissue, wherein a needle is advanced beyond the external elastic lamina of the blood vessel to inject the therapeutic cells.

20. The method of claim 19, wherein the peripheral blood vessel is a peripheral artery.

21. The method of claim 19, wherein injecting comprises advancing the needle from a lumen of the peripheral blood vessel to the location beyond the endothelium and infusing the therapeutic cells through the needle.

22. The method of claim 19, wherein the therapeutic cells are selected from the group consisting of stem cells, cardiomyocytes, fibroblasts, endothelial cells, skeletal myoblasts, mesenchymal stem cells, cells from unprocessed or minimally processed bone marrow, peripheral blood stem cells, and mobilized peripheral blood stem cells.

23. The method of claim 19, wherein the therapeutic cells are pluripotent stem cells.

24. The method of claim 23, wherein the pluripotent stem cells are mesenchymal adult progenitor cells.

* * * * *